United States Patent [19]

Kawai et al.

[11] 4,350,594
[45] Sep. 21, 1982

[54] BLOOD PURIFICATION USING PLURAL ULTRAFILTRATION STAGES

[75] Inventors: Syuji Kawai, Kurashiki; Tadayuki Yamane, Kyoto; Michio Abe, Saiki; Toshihiko Ono, Oita; Shuji Yamauchi, Saiki, all of Japan

[73] Assignees: Kuraray Co., Ltd., Kurashiki; Kawasumi Laboratories, Inc., Tokyo, both of Japan

[21] Appl. No.: 252,245

[22] Filed: Apr. 8, 1981

[30] Foreign Application Priority Data

Apr. 16, 1980 [JP] Japan ................................. 45-50735
Apr. 16, 1980 [JP] Japan ................................. 45-50736

[51] Int. Cl.³ .................... B01D 13/00; B01D 31/00
[52] U.S. Cl. .................................. 210/637; 210/641; 210/651; 210/110; 210/137; 210/259; 210/295; 210/433.2
[58] Field of Search .............. 210/637, 641, 645–651, 210/741, 109, 110, 137, 252, 257.2, 259, 295, 321, 433.2

[56] References Cited

U.S. PATENT DOCUMENTS 3,579,441 5/1971 Brown ........................... 210/641 X
3,946,731 3/1976 Lichtenstein .................... 210/87 X

OTHER PUBLICATIONS

Pasternack, A., "Engineering Aspects of Artificial Kidney Development and Operation", Intern. Chem. Eng., vol. 16, No. 1, Jan. 1976, pp. 1–10.

Primary Examiner—David R. Sadowski
Attorney, Agent, or Firm—Barry Kramer

[57] ABSTRACT

The invention provides a blood treatment apparatus realizing double-step-membrane filtration, namely separation of blood into plasma and a corpuscular fraction and separation of high-molecular-weight substances (e.g. gamma-globulin) in the plasma from low-molecular-weight substances (e.g. albumin). A method of treating blood is also provided.

The apparatus and method are effective e.g. in the treatment of blood of patients with peripheral circulatory insufficiency due to arteriosclerosis and of patients with rheumatoid arthritis, which is an autoimmune disease.

12 Claims, 3 Drawing Figures

BLOOD PURIFICATION USING PLURAL ULTRAFILTRATION STAGES

BACKGROUND OF THE INVENTION

1. Field of the Invention

This invention relates to a blood treatment apparatus with an extracorporeal circuit, and more particularly to a blood treatment apparatus wth two membrane modules different in performance. It also relates to a method of treating blood.

2. Description of Prior Art

Various blood treatment techniques such as hemodialysis using a dialysis membrane, hemofiltration with a filtration membrane and hemoperfusion with an adsorbent, among others, have come into wide clinical use. Recently, a technique called plasmapheresis, which is one of the extracorporeal blood treatment techniques, has been developed. Said plasmapheresis comprises first separating blood into plasma and corpuscular components and then treating the plasma by a certain technique, thereby removing pathogenic factors. More specifically, plasmapheresis includes the plasma exchange method in which the plasma is exchanged for a plasma preparation and the specific plasma component permeation method which comprises further fractionating the plasma, removing the problematic fraction and returning the remaining fractions, together with the corpuscular components, to the circulation. When viewed as a therapeutic means, the plasma exchange method is not always preferable because the whole amount of the plasma should be exchanged. This requires a large amount of a plasma to be prepared at great expense. Also, when using the plasma exchange method, adverse effects may be produced due to incomplete supplementation of various physiologic substances contained in the plasma. On the contrary, the specific plasma component permeation method can be regarded as a more desirable therapeutic means, since only a part of the plasma is discarded while the rest is returned to the circulation, substantially overcoming the two problems mentioned above.

Pioneer studies of the specific plasma component permeation method have already been made and described. For example, there is a report by T. Agishi et al, published in the *Japanese Journal of Medical Instrumentation*, vol. 49, Supplement, p. 259-261 (1979). Also, a Japanese patent application laid open under No. 2444/1980 discloses a blood treatment apparatus in which a specific plasma component permeation method is realized in combination with a water-removing means.

However, these techniques known in the art, though called techniques, are no more than proposals of possibilities or theoretical apparatus. No invention can be found therein for an apparatus useful in medical practice.

SUMMARY OF THE INVENTION

The present inventors, with assistance from the above T. Agishi et al., have conducted intensive research on the specific plasma component permeation method using a membrane, and have succeeded in developing a system apparatus which can be put to practical use.

The present invention provides a blood treatment apparatus with a first and a second membrane module, comprising a blood inlet circuit including a pump $M_1$, a membrane module for plasma separation connected to said blood inlet circuit (first membrane module), a plasma outlet circuit for the plasma separated by the first membrane module, including a pressure gauge $P_2$ and a pump $M_2$, and a membrane module for plasma fractionation (second membrane module) which fractionates the plasma coming from the plasma outlet circuit into two components. A plasma fraction outlet circuit including pump $M_3$ is provided for the high-molecular-weight fraction separated by the second membrane module. Also provided is a blood return circuit for receiving the low-molecular-weight fraction separated by the second membrane module, which circuit is united with a blood corpuscles outlet circuit for adding the corpuscular components separated by the first membrane module, through valve $V_1$, and returning the treated blood to the circulation. The pressure of the plasma outlet circuit is indicated by pressure gauge $P_2$. This pressure is adjusted so as not to become negative, the ratio of the amount of the plasma flowing into the second membrane module to that of the plasma fraction to be expelled being adjusted to a predetermined value by controlling the flow rate ratio between pump $M_2$ and pump $M_3$.

BRIEF DESCRIPTION OF THE DRAWINGS

In the accompanying drawings, each of FIGS. 1, 2 and 3 is a schematic representation of a different embodiment of the blood treatment apparatus in accordance with the present invention.

DETAILED DESCRIPTION OF THE INVENTION

Figure 1:
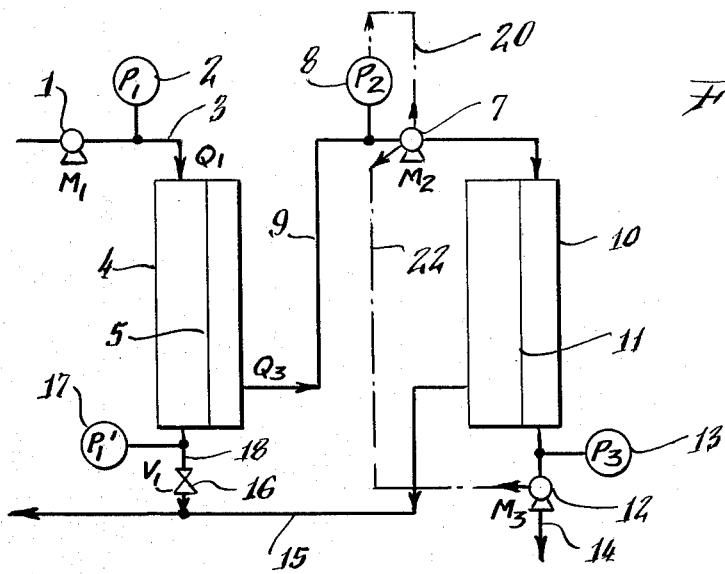

In accordance with the present invention, separation of blood into plasma and corpuscular components and separation of the plasma into a high-molecular-weight and a low-molecular-weight fraction are carried out using two membrane modules of different kinds. One of these modules is called a plasma separation membrane module ("first membrane module") and the other is called a plasma fraction fractionation membrane module ("second membrane module"). The membrane to be used in the first membrane module, i.e., to be used for separating corpuscular components from plasma, is a microporous membrane having an average effective pore size of 0.02–0.4 micron, preferably about 0.1 micron. Preferably, this membrane will be a homogeneous microporous membrane, a microfiltration membrane or a so-called asymmetrical membrane comprising a porous supporting layer and a relatively dense microporous layer. Pore sizes larger than 0.4 micron often lead to hemolysis, whereas pore sizes smaller than 0.02 micron cut off such proteins as gamma-globulin, and therefore cannot be used to give a plasma containing these proteins. Examples of such membrane are substantially uniform microporous membranes made of polyvinyl alcohol (PVA) type polymers, separately developed by one of the present inventors, as well as other substantially uniform microporous membranes and asymmetrical membranes made of ethylene-vinyl alcohol (EVA) copolymers, cellulose derivatives (e.g. cellulose acetates), polyolefins, polyacrylonitriles, polyamides, polyesters, polysulfones, and so on. Preferred among these are PVA, EVA, cellulose derivative and polysulfone membranes, which have good biocompatibility.

The membrane used in the second membrane module separates plasma into a high-molecular-weight fraction and a low-molecular-weight fraction. The boundary molecular weight can optionally be set depending on the desired purpose. The apparatus of the present invention can be used in the treatment of autoimmune diseases and thus, in one embodiment, the molecular-weight cut-off boundary can be set at 100,000. Pathogenic substances in autoimmune diseases are often present in the form bound to gamma-globulin having a molecular weight of about 160,000. Therefore, it is desirable that substances having molecular weights of about 160,000 and higher be removed but substances having lower molecular weights such as albumin (molecular weight=67,000) useful to the organism be returned. Thus, setting the boundary molecular weight at 100,000 can result in rigid separation of the above-mentioned gamma-globulin and albumin. The boundary of molecular-weight cut-off should be selected depending on the molecular weight of the pathogenic substance to be removed, and in another case where an immune complex is the causative factor, it is set at 100,000–200,000.

As the second membrane, there can be used any membrane that can fractionate plasma under pressure. In this sense, membranes having ultrafiltration capacity can widely be used. No special limitations are placed on the membrane structure, and the above-mentioned uniform microporous membranes, asymmetrical membranes and uniform gel membranes can be used. The term "uniform gel membranes" as used herein means membranes having substantially no micropores or tiny gap structures among joined particles when observed in the dry or wet state under an electron microscope at a magnification of 24,000.

The membranes mentioned above are used in the form of flat membranes or hollow fiber membranes and constitute membrane modules. In view of the simplicity of module preparation and the possibility of miniaturization, hollow fiber membranes are preferred.

FIG. 1 is a schematic representation of an example of the blood treatment apparatus in accordance with the present invention. Referring to FIG. 1, blood is pumped through blood inlet circuit 3 equipped with pump $M_1$ (1) and preferably also pressure gauge $P_1$ (2) into plasma separation membrane module 4, where membrane 5 separates the blood into plasma and corpuscular components. The plasma separated is pumped through plasma outlet circuit 9 equipped with pressure gauge $P_2$ (8) and pump $M_2$ (7) into plasma fractionation membrane module 10. In the second membrane module, the plasma is fractionated by membrane 11, and the high-molecular-weight fraction is expelled from the system through plasma fraction outlet circuit 14 equipped with pump $M_3$ (12) and preferably also pressure gauge $P_3$ for monitoring (13). The low-molecular-weight fraction which has permeated membrane 11 flows out through blood return circuit 15. The corpuscular components coming from first membrane module 4 run through corpuscles outlet circuit 18 equipped with valve $V_1$ (16) and preferably also pressure gauge $P_1'$ for monitoring (17) and are combined with the low-molecular-weight plasma fraction coming through blood return circuit 15, to be returned to the organism.

FIG. 1 shows only those constituents that are essential in the practice of the present invention. A drip chamber, a blood filter, a heparin infusion circuit, another plasma treatment module such as an activated carbon column and so forth may be added thereto.

In the apparatus as shown in FIG. 1, the pressure indicated by pressure gauge $P_2$ (8) is adjusted to a predetermined constant value by correlating pressure gauge $P_2$ (8) with pump $M_2$ (7), so that it can never become substantially negative. This correlation is shown by dashed line 20. For example, the number of revolutions of pump $M_2$ is adjusted by an electric signal corresponding to the pressure indication of pressure gauge $P_2$ so that the pressure on $P_2$ can be kept constant. A characteristic feature of the apparatus of the present invention is that the apparatus is constructed so as to maintain the pressure in the plasma outlet circuit at a constant level. Since the pressure exerted on blood in the first membrane module is kept constant, blood corpuscles are prevented from being damaged. It is also desirable that the pressure $P_1$ exerted on the blood by first pump $M_1$ (1) be maintained at levels not exceeding a certain value, generally at 150 mmHg or below, preferably at 100 mmHg or below. When ease of handling is taken into consideration, the lowest limit value for $P_1$ is about 0 mmHg. In addition to such conditions, it is necessary to prevent the pressure on $P_2$ in the plasma outlet circuit from becoming substantially negative. The pressure which is not substantially negative is $-40$ mmHg, preferably $-20$ mmHg to 20 mmHg. It is desirable that the pressure be in the neighborhood of 0 mmHg, i.e., atmospheric pressure. Were the pressure on $P_2$ to become more negative, a negative pressure would be exerted on first membrane 5 and the transmembrane pressure (TMP) would increase. Such an increase in TMP would make the differential pressure exerted on the corpuscular components on the membrane surface greater, thereby increasing the risk of corpuscles being damaged. Therefore, such excessively negative pressure on $P_2$ should be avoided. The TMP should preferably be not greater than 100 mmHg. Furthermore, a secondary effect possibly produced by a negative pressure in a blood treatment apparatus is that, if a part of the circuit should be connected loosely, a foreign substance such as air would be allowed to penetrate into the circuit from the outside, which may lead to serious consequences. Thus, adjustment of pressure on $P_2$ so as not to become substantially negative is also desirable to prevent such an accident.

Both first membrane 5 and second membrane 11 change in performance with time due to adhesion of proteins and so on during blood treatment. Therefore, when the blood pressure exerted on membrane 5 is kept constant, the amount of plasma separated ($Q_3$) changes with time. Since the second membrane module fractionates plasma under pressure, a change in amount of plasma entering the second membrane module will cause a change in the pressure condition and consequently a change in fractionation performance of the second membrane module. Such a change must be avoided at any cost. To accomplish this, the flow rate ratio between pump $M_2$ (7) and pump $M_3$ (12) must be adjusted to a constant value so that the pressure in the second membrane module can be kept constant even if the plasma amount $Q_3$ is changing. The correlation between pumps $M_2$ and $M_3$ is shown by dashed line 22. Furthermore, for safety reasons, it is desirable to provide the plasma fraction outlet circuit with pressure gauge $P_3$ (13) for directly monitoring the pressure in the second membrane module.

With a blood treatment apparatus constructed in the above manner, very good results can be obtained with minimum harm to the blood, since it is now possible to treat blood in a stable manner under conditions which produce a constant pressure on blood, without any substantial change in fractionation behavior of plasma.

Figure 2:
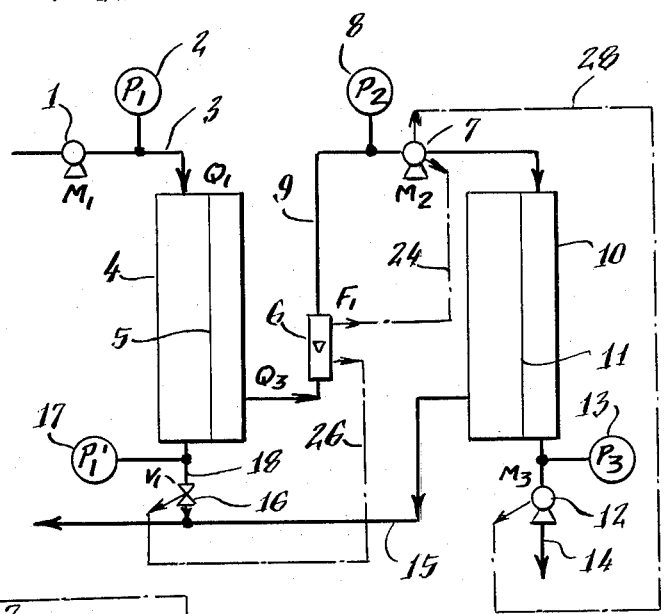

FIG. 2 is a schematic representation of another example of the blood treatment apparatus in accordance with the present invention. Referring to FIG. 2, blood is pumped through blood inlet circuit 3 equipped with pump $M_1$ (1) and preferably also with pressure gauge $P_1$ (2) into plasma separation membrane 4, where the blood is separated into plasma and a corpuscular fraction by membrane 5. The plasma separated is pumped through plasma outlet circuit 9 equipped with flowmeter $F_1$ (6), pump $M_2$ (7) and preferably also pressure gauge $P_2$ (8) into plasma fractionation membrane module 10. In the second membrane module, the plasma is fractionated by membrane 11, and the high-molecular-weight fraction is expelled through plasma fraction outlet circuit 14 equipped with pump $M_3$ (12) and preferably also with pressure gauge $P_3$ (13). The low-molecular-weight fraction which has permeated membrane 11 is led out of the second membrane module through blood return circuit 15. The corpuscular fraction coming from first membrane module 4 runs through corpuscles outlet circuit 18 equipped with valve $V_1$ (16) and preferable also with pressure gauge $P_1'$ (17) and is combined with the low-molecular-weight plasma fraction coming through blood return circuit 15, and the mixture is returned to the circulatory system of the organism.

FIG. 2 shows only those constituents that are essential in the practice of the present invention. A drip chamber, a blood filter, a heparin infusion circuit, another plasma treatment module such as activated carbon and so forth may optionally be added. In the apparatus shown in FIG. 2, the amount or rate of flow, $Q_3$, of plasma coming from first membrane module 4 is adjusted to a predetermined value by controlling valve $V_1$ (16) and flowmeter $F_1$ (6) in association with each other. This cooperation is shown by dashed line 26. Thus, valve 16 is adjusted by an appropriate means so that flowmeter 6 may indicate a constant value. For example, opening and closing of valve 16 may be controlled by an electric signal corresponding to the data furnished by the flowmeter. What is important with the first membrane module is that, in the plasma separation, damaging of blood corpuscles and consequential hemolysis can be prevented. To this end, the pressure $P_1$ (2) produced by first pump $M_1$ (1) is adjusted to 150 mmHg or below, preferably 100 mmHg or below. The lowest limit value is, as mentioned previously, about 0 mmHg. For observing the change of said pressure, it is preferable to provide pressure gauge $P_1$ (2). Both first membrane 5 and second membrane 11 change in performance with time due to adhesion of proteins and so on during blood treatment. Therefore, even when the blood pressure on membrane 5 is kept constant, the amount of plasma separated, $Q_3$, changes with time. To solve such a problem, it is necessary to provide flowmeter $F_1$ for directly monitoring plasma amount $Q_3$ in the plasma outlet circuit.

A characteristic feature of the apparatus of the present invention is that the apparatus is constructed so as to maintain plasma amount $Q_3$ at a constant level. This feature is in common with other embodiments of the invention to be mentioned later. When blood is treated at a constant plasma flow rate ($Q_3$), the subsequent plasma fractionation can also be effected at a constant flow rate, so that blood treatment can be conducted as scheduled, therefore very efficiently from the viewpoint of therapeutic practice.

Furthermore, in the apparatus shown in FIG. 2, the pressure in plasma outlet circuit 9 ($P_2$) must be adjusted so as not to become substantially negative by controlling flowmeter $F_1$ (6) and pump $M_2$ (7) in association with each other, as shown by dashed line 24. A negative pressure in circuit 9 produces a negative pressure on first membrane 5, whereby the transmembrane pressure (TMP) increases and consequently the differential pressure acting on the blood corpuscles on the membrane surface increases. The result is an increase in the risk of corpuscles being damaged, which should be avoided. As mentioned previously, the TMP should preferably be not greater than 100 mmHg. Furthermore, a secondary effect possibly produced by a negative pressure part present in a blood treatment apparatus like the one in accordance with the invention is that, if loosely connected parts should be present in the circuit, a foreign matter such as air would penetrate into the circuit from the outside, which may lead to serious consequences. For prevention of such an accident, it is required that adjustment be made so as not to allow a negative pressure by controlling flowmeter $F_1$ (6) and pump $M_2$ (7) in association with each other. The pressure which is not substantially negative is a pressure not lower than $-40$ mmHg, preferably not lower than $-20$ mmHg. The upper limit is 40 mmHg or below, preferably 20 mmHg or below. A pressure in the neighborhood of 0 mmHg, i.e., atmospheric pressure, is desirable.

The plasma introduced into plasma fractionation membrane module 10 is fractionated by membrane 11. Thus, the low-molecular-weight components permeate the membrane, while the high-molecular-weight components are excluded and expelled from the system through pump $M_3$. If the amount of plasma introduced, $Q_3$, is constant, the amount of permeating components is determined by the amount of high-molecular-weight components that are expelled. Therefore, the amount of low-molecular-weight components to be sent to the blood return circuit can be adjusted through the feed rate ratio between pump $M_2$ and pump $M_3$. Such relationship between pump $M_2$ and pump $M_3$ is designated by dashed line 28. Accordingly, in accordance with the present invention, the ratio of the amount of plasma which is introduced into module 10 to the amount of plasma which is withdrawn from said module is adjusted by controlling the flow rate ratio between pump $M_2$ (7) and pump $M_3$ (12). It is preferable to provide pressure gauge $P_3$ (13) in the plasma fraction outlet circuit for monitoring the pressure in said circuit.

The low-molecular-weight components which have permeated second membrane 11 run through blood return circuit 15 and are combined by the corpuscular fraction from corpuscles outlet circuit 18 and returned to the organism.

Figure 3:
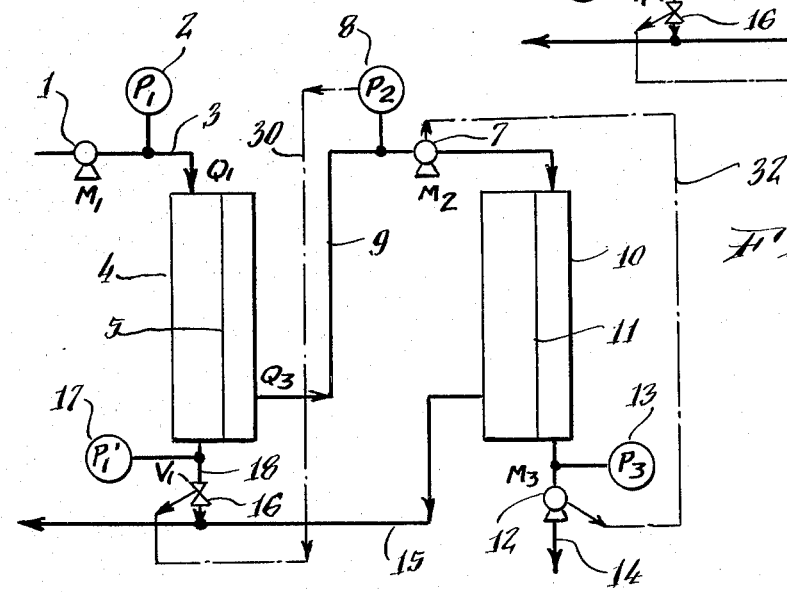

FIG. 3 is a schematic representation of another blood treatment apparatus in accordance with the present invention. As is evident on comparison between FIG. 2 and FIG. 3, both the apparatus shown therein have common parts, with respect to which repeated description is avoided.

The plasma fraction separated in first membrane module 4 is sent out into plasma outlet circuit 9 equipped with pressure gauge $P_2$ (8) and pump $M_2$ (7). As compared with the apparatus shown in FIG. 2, the apparatus shown in FIG. 3 differs in that flowmeter $F_1$ is absent and pressure gauge $P_2$ is essential. In this apparatus, too, pump $M_2$ (7) is adjusted so that the plasma outlet amount, $Q_3$, can be kept at a predetermined value.

Furthermore, pressure gauge $P_2$ (8) and valve $V_1$ (16) are controlled in association with each other (dashed line 30) so that the pressure within plasma outlet circuit 9 cannot become substantially negative. In addition, the plasma fractionation rate in the second membrane module is controlled by controlling the flow rate ratio between pump $M_2$ (7) and pump $M_3$ (12), as shown by dashed line 32. The apparatus shown in FIG. 3 is composed of a smaller number of constituent parts as compared with the apparatus shown in FIG. 2, and has a simplified control circuit, and therefore, reduction in manufacturing cost and facility of operation are expected.

Using at least pump $M_2$ for adjusting the plasma pressure so as not to become substantially negative, the pressure adjustments set forth above and in FIGS. 1, 2 and 3 are the preferred embodiments, but the following pressure adjustments may also be used in this invention:

(a) pressure adjustment without controlling flowmeter $F_1$ (6) and pump $M_2$ (7) in association with each other in FIG. 2;

(b) pressure adjustment controlling pressure gauge $P_2$ (8) and pump $M_2$ (7) in association with each other instead of controlling flowmeter $F_1$ (6) and pump $M_2$ (7) in association with each other in FIG. 2;

(c) pressure adjustment controlling pressure gauge $P_2$ (8) and pump $M_2$ (7) in association with each other in FIG. 3.

Furthermore, in accordance with the present invention, for supplementing that portion of plasma that has been removed in second filter 10, an albumin solution or hydroxy ethyl starch (HES) or other substitute fluids can be added to the treated plasma for introduction into the body of a patient. In the practice of the present invention, in introducing such a substitute fluid, it is preferable that the rates of flow through the pump for substitute fluid introduction and pump $M_3$ (12) provided in high-molecular-weight fraction outlet circuit 14 be controlled in association with each other so that the amount of the high-molecular-weight fraction withdrawn is equal to the amount of the substitute fluid introduced. The substitute fluid must not be introduced into the body in too large or too small a quantity.

In practicing the present invention, the associated control of pump $M_2$ (7) and pump $M_3$ (12) or of pump $M_3$ (12) and the pump for substitute fluid introduction is preferably done electrically. Another possibility is that different inside diameters be given to the tubes connected to the respective pumps, and then squeezing the tubes by a single driving roller, whereby the flow rates can be adjusted according to the respective tube diameters.

The treatment system of the present invention can effectively be used in the treatment of the blood of patients with the following disorders: autoimmune hemolytic anemia, idiopathic thrombocytopenic purpura, chronic glomerulonephritis, Goodpasture syndrome, systemic lupus erythematosus, progressive systemic sclerosis, etc.

The following examples further illustrate the present invention:

EXAMPLE 1

A first membrane module was constructed by incorporating into a cylindrical cartridge a polyvinyl alcohol hollow fiber membrane having a substantially uniform microporous structure with an average pore size of 0.04 micron, an inside diameter of 400 microns and membrane thickness of 200 microns, the membrane area being 0.15 $m^2$. A second membrane module was prepared by incorporating into a cylindrical cartridge an ethylene-vinyl alcohol copolymer (EVA) hollow fiber membrane having an asymmetrical structure comprising a porous support layer and a microporous layer with an average micropose diameter of 110 Ångstroms, an inside diameter of 330 microns and a membrane thickness of 45 microns as disclosed in Japanese Patent Application Kokai (laid open) No. 35,969/1980, the membrane area being 0.9 $m^2$. These membrane modules were built into the circuit shown in FIG. 1, and the blood of a patient with peripheral circulatory disturbance due to corticotropin releasing factor (CRF) and arteriosclerosis was treated.

For plasma separation in the first membrane module, the blood flow rate through pump $M_1$ was adjusted to 110 ml/minute, and, furthermore, the pressure on $P_1$ was maintained at 90 mmHg by adjusting valve $V_1$. The rate of flow of the plasma separated was about 30 ml/minute at the early stage but dropped to 20 ml/minute with the lapse of time. However, pump $M_2$ and pressure gauge $P_2$ were controlled in association with each other while monitoring by means of pressure gauge $P_2$, so that gauge $P_2$ always indicated a pressure within the range of 0 to $-20$ mmHg. In addition, pump $M_3$ and pump $M_2$ were controlled in association with each other, so that the flow rate ratio therebetween was always 1:4. In this manner, the blood could be treated continuously for two hours. As a result, the percent immunoglobulin removal from the blood of the patient was 23%.

EXAMPLE 2

A first membrane module was constructed by incorporating a polyvinyl alcohol hollow fiber membrane having a substantially uniform microporous structure with an average pore size of 0.04 micron, an inside diameter of 400 microns and a membrane thickness of 200 microns into a cylindrical cartridge, the membrane area being 0.15 $m^2$. Separately, a second membrane module was constructed by incorporating into a cylindrical cartridge an EVA hollow fiber membrane having an asymmetric structure comprising a porous support layer and a microporous layer with an average micropore diameter of 110 Ångstroms, an inside diameter of 330 microns and a membrane thickness of 45 microns (cf. Japanese Patent Application Kokai No. 35,969/1980), the membrane area being 0.9 $m^2$. These membrane modules were built into the circuit shown in FIG. 2, and the blood of a patient with peripheral circulatory disturbance due to CRF and arteriosclerosis was treated.

For plasma separation in the first membrane module, plasma outlet rate $Q_3$ was adjusted to 24 ml/minute on the average by controlling pump $M_2$ while monitoring flowmeter $F_1$, and in addition, pump $M_1$ and valve $V_1$ were respectively adjusted so that pressure gauge $P_1$ always indicated 100 mmHg. The blood flow rate, $Q_1$, was in the neighborhood of 100 ml/minute. The pressure gauge always indicated a pressure within the range of 0 to $-20$ mmHg.

For fractionation of the plasma components coming from the first membrane module at a rate of 24 ml/minute into the second membrane module, the flow rate ratio between pump $M_2$ and pump $M_3$ was adjusted to 4:1. Thus, the rate of discharge flow through pump $M_3$ was about 6 ml/minute. The low-molecular-weight plasma fraction permeated the second membrane at a rate of 18 ml/minute, and was combined with the concentrated corpuscular fraction and returned to the patient. After continuous blood treatment in this manner for three hours, the percent immunoglobulin removal from the blood of the patient was 34%, and almost no changes were observed in electrolytes. After the outbreak of the disease, the patient had complained of a pain in the toe tip, but after one blood treatment with this apparatus, the patient was free from such pain.

EXAMPLE 3

The same membrane modules (first and second) as used in Example 2 were built into the circuit shown in FIG. 3 for treating the blood of a patient with rheumatoid arthritis, an autoimmune disease. For plasma separation in the first membrane module, the blood flow rate ($Q_1$) was adjusted to 120 ml/minute by controlling pump $M_1$, and the feed rate through pump $M_2$ was adjusted to 22 ml/minute. Furthermore, a circuit was provided for control of valve $V_1$ in association with pressure gauge $P_2$ such that valve $V_1$ was operated so as to maintain the indication of gauge $P_2$ within the range of 0 to $-20$ mmHg. The indication of pressure gauge $P_1$ at that time was 80 mmHg. Hemolysis observed in this plasma separation procedure was 1 mg/dl as free hemoglobing. Thus, good plasma separation was achieved with almost no substantial hemolysis.

The plasma sent out by pump $M_2$ was deprived of high-molecular-weight fraction components in the second membrane module, then combined with the concentrated blood corpuscular fraction and returned to the patient. In this second membrane filtration, analysis revealed that the ratio between albumin and gamma-globulin (A/G) in the fluid expelled out of the system by pump $M_3$ was 0.4. When compared with the ratio A/G (0.6) for the plasma before filtration, this analytical result clearly indicates that a considerable amount of gamma-globulin was removed from the blood.

The flow rate ratio between pump $M_2$ and pump $M_3$ was adjusted to 4:1. Thus, the rate of discharge flow through pump $M_3$ was about 5:5 ml/minute. The low-molecular-weight plasma fraction permeated the second membrane at a rate of 16.5 ml/minute, and was combined with the concentrated corpuscular fraction and returned to the patient.

What is claimed is:

1. A blood treatment apparatus with a first and a second membrane module, said apparatus comprising
   a blood inlet circuit including a first pump, a first membrane module means including a semipermeable membrane having pores of a size for retaining a blood corpuscular fraction and for permeation of a plasma fraction connected to said blood inlet circuit,
   plasma outlet circuit means for the plasma separated by the first membrane module means, said plasma outlet circuit means including a pressure adjustment unit comprising at least a second pump means for adjusting the plasma pressure so that is is within the range of from about $-40$ mmHg to 40 mmHg
   a second membrane module means including a semipermeable membrane having pores of a size to permeate human blood serum albumin for plasma fractionation which fractionates the plasma from said plasma outlet circuit means into two fractions,
   plasma fraction outlet circuit means for expelling a high-molecular-weight fraction separated in the second membrane module means, said fraction outlet circuit means including a third pump positioned downstream of said second membrane module means
   blood return circuit means for receiving a low-molecular weight fraction containing human blood urum albumin separated in the second membrane module means and combining the same with blood corpuscular fraction separated in the first membrane module means, and
   means for controlling the ratio between the rate of flow of the plasma flowing into the second membrane module means and the rate of the plasma fraction to be expelled from same to a predetermined value by controlling the flow rate ratio between said second and third pumps.

2. The blood treatment apparatus of claim 1, wherein the pressure adjustment unit includes a pressure gauge; and means for controlling said second pump so as to prevent the pressure in the plasma outlet circuit means as indicated by said gauge from deviating from said range.

3. The blood treatment apparatus of claim 1 or 2 wherein the pressure in the plasma outlet circuit means is adjusted to $-20$ mmHg to 20 mmHg.

4. A blood treatment apparatus with a first and a second membrane module, comprising:
   a blood inlet circuit including a first pump,
   a first membrane module means including a semipermeable membrane having pores for a size for retaining a blood corpuscular fraction and for permeation of a plasma fraction connected to said blood inlet circuit,
   plasma outlet circuit means for the plasma separated by the first membrane module means, including a flowmeter and a second pump,
   a second membrane module means including a semipermeable membrane having pores of a size to permeate human blood serum albumin for plasma fractionation which fractionates the plasma from the plasma outlet circuit means into two fractions,
   plasma fraction outlet circuit means for expelling a high-molecular-weight fraction separated in the second membrane module means, said fraction outlet circuit means including a third pump positioned downstream of said second membrane module means, and
   blood return circuit means for receiving a low molecular-weight fraction containing human blood serum albumin separated in the second membrane module means and combining same with the blood corpuscular fraction separated in the first membrane module means, said blood return circuit means including a valve, means for controlling said valve in association with said flowmeter for maintaining the pressure in the plasma outlet circuit means within a range of about $-40$ mmHg to 40 mmHg,
   means for controlling the flow rate ratio between said second pump and said third pump so as to adjust the flow rate ratio between the plasma introduced into the second membrane module means and the plasma fraction to be expelled from same to a predetermined value.

5. A blood treatment apparatus with a first and a second membrane module, comprising:

a blood inlet circuit including a first pump, a first membrane module means including a semipermeable membrane having pores of a size of retaining a blood corpuscular fraction and for permeation of a plasma fraction connected to said blood inlet circuit, plasma outlet circuit means for the plasma separated in the first membrane module means, said plasma outlet circuit means including a pressure gauge and a second pump means, a second membrane module means including a semipermeable membrane having pores of a size to permeate human blood serum albumin for plasma fractionation which fractionates the plasma from the plasma outlet circuit means into two fractions, plasma fraction outlet circuit means for expelling a high-molecular-weight fraction separated in the second membrane module means, said plasma fraction outlet circuit means including a third pump positioned downstream of said second membrane module means, blood return circuit means for receiving a low molecular-weight fraction containing human blood serum albumin separated in the second membrane module means and combining it with the blood corpuscular fraction separated in the first membrane module means, said blood return circuit including a valve, means for controlling said second pump so as to adjust the rate of flow of plasma from the first membrane module means to a predetermined rate, means for controlling said valve in association with said pressure gauge so as to maintain the pressure in the plasma outlet circuit means within a range of about −40 mmHg to 40 mmHg, and means for controlling the flow rate ratio between the plasma flowing into the second membrane module means and the plasma fraction to be expelled from same to a predetermined value by controlling the flow rate ratio between said second pump and said third pump.

6. The blood treatment apparatus of claim 4 or 5 wherein the pressure in the plasma outlet circuit means is adjusted to −20 mmHg to 20 mmHg.

7. A method of treating blood comprising: separating plasma from the blood in a first membrane module utilizing a semipermeable membrane having pores of a size retaining a blood corpuscular fraction and permeating a plasma fraction pumping said plasma through a plasma outlet circuit having a first pump, adjusting the plasma pressure in said plasma outlet circuit to maintain said pressure in a range from about −40 mmHg to 40 mmHg, fractionating said plasma in a second membrane module into two fractions utilizing a semipermeable membrane having pores of a size permeating a human blood serum albumin fraction expelling a high-molecular-weight fraction separated in the second membrane module through a plasma fraction outlet circuit having a second pump positioned downstream of said second membrane module, combining the low-molecular-weight fraction containing human blood serum albumin separated in said second membrane module with the blood corpuscular fraction separated in said first membrane module, and adjusting the ratio between the rate of flow of the plasma flowing into said second membrane module and the rate of plasma fraction being expelled from said second membrane module to a predetermined value by controlling the flow rate between said first and second pumps.

8. The method of claim 7 wherein the pressure in said plasma outlet circuit is adjusted to between −20 mmHg and 20 mmHg.

9. A method of treating blood comprising:

separating plasma from the blood in a first membrane module utilizing a semipermeable membrane having pores of a size retaining a blood corpuscular fraction and permeating a plasma fraction, pumping said plasma through a plasma outlet circuit including a flowmeter and a first pump, fractionating said plasma in a second membrane module into two fractions utilizing a semipermeable membrane having pores of a size permeating human blood serum albumin, expelling a high-molecular-weight fraction separated in the second membrane module through a plasma fraction outlet circuit having a second pump positioned downstream of said second membrane module, combining, in a blood return circuit having a valve, the low-molecular-weight fraction containing human blood serum albumin separated in said second membrane module with the blood corpuscular fraction separated in said first membrane module, controlling said valve in association with said flowmeter so as to maintain the pressure in said plasma outlet circuit within a range of from about −40 mmHg to 40 mmHg, and adjusting the ratio between the rate of flow of the plasma flowing into said second membrane module and the rate of plasma fraction being expelled from said second membrane module to a predetermined value by controlling the flow rate between said first and second pumps.

10. The method of claim 9 wherein the pressure in said plasma outlet circuit is adjusted to between −20 mmHg and 20 mmHg.

11. A method of treating blood comprising:

separating plasma from the blood in a first membrane module utilizing a semipermeable membrane having pores of a size retaining a blood corpuscular fraction and permeating a plasma fraction, pumping said plasma through a plasma outlet circuit having a first pump and a pressure gauge, fractionating said plasma in a second membrane module into two fractions utilizing a semipermeable membrane having pores of a size permeating human blood serum albumin, expelling a high-molecular-weight fraction separated in the second membrane module through a plasma fraction outlet circuit having a second pump positioned downstream of said second membrane module, combining, in a blood return circuit having a valve, the low-molecular-weight fraction containing human blood serum albumin separated in said second membrane module with the blood corpuscular fraction separated in said first membrane module, controlling said first pump so as to adjust the rate of flow of plasma from the first membrane module to a predetermined rate, controlling said valve in association with said pressure gauge so as to maintain the pressure in said plasma outlet circuit in a range from about −40 mmHg to 40 mmHg, and adjusting the ratio between the rate of flow of the plasma flowing into said second membrane module and the rate of plasma fraction being expelled from said second membrane module to a predetermined value by controlling the flow rate between said first and second pumps.

12. The method of claim 11 wherein the pressure in said plasma outlet circuit is adjusted to between −20 mmHg and 20 mmHg.

* * * * *

UNITED STATES PATENT AND TRADEMARK OFFICE
CERTIFICATE OF CORRECTION

PATENT NO. : 4350594

DATED : September 21, 1982

INVENTOR(S) : Syuji Kawai et al.

It is certified that error appears in the above-identified patent and that said Letters Patent is hereby corrected as shown below:

In Claim 1, Column 10, line 9 of the Patent, change "urum" to --serum--.

In Claim 5, Column 11, line 3 of the Patent, delete "of" before "retaining" and substitute --for-- therefor.

In Claim 4, Column 10, line 32, delete "for" after "pores" and substitute -- of -- therefor.

Signed and Sealed this

Twenty-fourth Day of May 1983

[SEAL]

Attest:

DONALD J. QUIGG

Attesting Officer

Acting Commissioner of Patents and Trademarks